US008821386B2

(12) United States Patent  
Park et al.

(10) Patent No.: US 8,821,386 B2
(45) Date of Patent: Sep. 2, 2014

(54) MICRO ROBOT SYSTEM AND CAPSULE ENDOSCOPE SYSTEM FOR EXAMINING A TUBULAR DIGESTIVE SYSTEM

(75) Inventors: Suk Ho Park, Gwangju (KR); Jong Oh Park, Gyeonggi-do (KR); Hyun Chul Choi, Jeollanam-do (KR); Kyung Rae Cha, Gwangju (KR); Se Mi Jeong, Jeollabuk-do (KR)

(73) Assignee: Industry Foundation of Chonnam National University, Gwangju (KR)

( * ) Notice: Subject to any disclaimer, the term of this patent is extended or adjusted under 35 U.S.C. 154(b) by 21 days.

(21) Appl. No.: 13/446,219

(22) Filed: Apr. 13, 2012

(65) Prior Publication Data

US 2013/0053641 A1 Feb. 28, 2013

(30) Foreign Application Priority Data

Aug. 25, 2011 (KR) .......................... 10-2011-0085161

(51) Int. Cl.
*A61B 1/04* (2006.01)
*A61B 19/00* (2006.01)
*A61B 1/00* (2006.01)

(52) U.S. Cl.
CPC ................. *A61B 19/22* (2013.01); *A61B 1/041* (2013.01); *A61B 1/00158* (2013.01); *A61B 2019/2257* (2013.01)
USPC .......................................... 600/118; 600/117

(58) Field of Classification Search
USPC ........................... 600/103, 117, 118, 160, 178
See application file for complete search history.

(56) References Cited

U.S. PATENT DOCUMENTS

| 4,757,290 A * | 7/1988 | Keren ........................... 333/219 |
| 2010/0179381 A1 | 7/2010 | Kawano et al. |
| 2010/0307517 A1 * | 12/2010 | Kawano et al. ............... 128/899 |
| 2011/0034766 A1 | 2/2011 | Tanaka |
| 2011/0054254 A1 * | 3/2011 | Reinschke ..................... 600/118 |

FOREIGN PATENT DOCUMENTS

| DE | 103 46 678 A1 | 5/2005 |
| EP | 2 189 104 A1 | 5/2010 |
| JP | 2009-268639 A | 11/2009 |
| KR | 10-2008-0079037 A | 8/2008 |
| KR | 10-2011-0052963 A | 5/2011 |

OTHER PUBLICATIONS

Choi et al., EMA system with gradient and uniform saddle coils for 3D locomotion of microrobot, Sensors and Actuators A 163 (2010) 410-417.*

* cited by examiner

*Primary Examiner* — Anhtuan T Nguyen
*Assistant Examiner* — Rynae Boler
(74) *Attorney, Agent, or Firm* — Rabin & Berdo, P.C.

(57) ABSTRACT

A micro robot system movable on three dimensional space includes a micro robot unit including a magnet module having a certain magnetization direction and configured to rotate and proceed along a wall by a processional rotating magnetic field, and an electromagnetic field generation unit configured to set an alignment direction of the micro robot unit to have a certain angle with respect to the magnetization direction and configured to generate a magnetic field in the alignment direction to drive the micro robot unit.

6 Claims, 7 Drawing Sheets

MICRO ROBOT SYSTEM AND CAPSULE ENDOSCOPE SYSTEM FOR EXAMINING A TUBULAR DIGESTIVE SYSTEM

PRIORITY

This application claims the benefit under 35 U.S.C. §119 a of a Korean patent application filed in the Korean Intellectual Property Office on Aug. 25, 2011 and assigned Serial No. 10-2011-0085161, and the entire disclosure of which is hereby incorporated by reference.

BACKGROUND OF THE INVENTION

1. Field of the Invention

The present invention relates to a micro robot system and a capsule endoscope system for examining a tubular digestive system, and more particularly, to a micro robot system and a capsule endoscope system for examining a tubular digestive system, in which a micro robot having a camera installed therein is drawn close to a wall of a tubular organ and driven to move, while rotating, in a straight line direction along a side surface of the wall of the tubular organ, thereby being capable of examining a disease on the wall of the organ with ease and accuracy.

2. Description of the Related Art

A conventional flexible streamlined endoscope, which is inserted through a mouth or anus to perform an examination, is difficult to handle and causes a patient's suffering. In order to solve these problems, a capsule endoscope, which is swallowed through the mouth and passed through a digestive system for examination by using peristalsis of the digestive system, is recently developed.

In an endoscope that is currently being commercialized and available for sale, the endoscope does not have a separate driving function and is moved through the peristalsis of the digestive system to obtain images of the digestive system. Here, since the capsule endoscope does not have a self-driving function and passively observes a front/rear of the capsule endoscope thereof, a disease on a wall of an organ may not be sufficiently observed when the organ has a lot of curvature.

Also, in case of an organ such as an esophagus or a small intestine that has a smaller diameter, a conventional capsule endoscope may move therein; however, in a part with a lot of curvature or an organ such as a large intestine that has a larger diameter, it is impossible for the conventional capsule endoscope to move therein. Also, since the conventional capsule endoscope moves only in a forward direction, it is difficult to detect a disease on the organ's wall.

In order to solve these problems, Japanese Patent Publication No. 2009-268639, titled "Capsule Endoscope," by Olympus Co. is directed to attaching a camera along a longitudinal direction of the capsule endoscope to detect the disease on the organ's wall; however, since the capsule endoscope does not have self-driving capability and can be moved only by the peristalsis of the digestive system, many limitations exist. In addition, Korean Patent Publication No. 10-2011-0052963, titled "Bi-directional Driving System for a Capsule Micro Robot," by Korea Institute of Science and Technology discloses a mobile object and a leg that is coupled with the mobile object to move the mobile object such that forward and backward movement is enabled, thereby improving mobility; however, the capsule endoscope is still not pressed close to the wall such that examining the disease is still difficult in case of the organ having a large diameter.

SUMMARY OF THE INVENTION

Accordingly, the present invention has been made in view of the above problems, and the present invention is to provide a micro robot system and a capsule endoscope system for examining a tubular digestive system in which a magnetization direction and an alignment direction of a micro robot maintain a certain angle therebetween, the micro robot is rotated when a processional rotating magnetic field with respect to the alignment direction is generated, and the microrobot is proceeded, when forces are respectively applied to the micro robot in the alignment direction and a direction perpendicular to the alignment direction, while rotating, in a forward direction while pressing a wall.

Also, the present invention is to provide a micro robot system and a capsule endoscope system for examining a tubular digestive system in which a camera is installed on a wall of a capsule cylinder of a micro robot along a longitudinal direction of the capsule cylinder of the micro robot to examine a disease on a wall of the tubular digestive system.

Further, the present invention is to provide a micro robot system and a capsule endoscope system for examining a tubular digestive system in which three pairs of fixed coils are used to allow a micro robot to freely align and rotate in any direction on three dimensions, a pair of fixed coils and a pair of rotational coils are used to generate a driving force in any direction with respect to a direction in which the micro robot is aligned, thereby generating a magnetic field.

In one aspect of the present invention, a micro robot system movable on three dimensions includes a micro robot unit including a magnet module having a certain magnetization direction and configured to rotate and proceed along a wall by a processional rotating magnetic field, and an electromagnetic field generation unit configured to set an alignment direction of the micro robot unit to have a certain angle with respect to the magnetization direction and configured to generate a magnetic field in the alignment direction to drive the micro robot unit.

In another aspect of the present invention, a capsule endoscope system movable on three dimensions includes a capsule endoscope unit including a magnet module having a certain magnetization direction and configured to rotate and proceed along a wall by a processional rotating magnetic field, an electromagnetic field generation unit configured to set an alignment direction of the micro robot to have a certain angle with respect to the magnetization direction and configured to generate a magnetic field in the alignment direction to drive the micro robot unit, and an imaging unit configured to receive and display images obtained by the capsule endoscope unit and a location of the capsule endoscope.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

The features and advantages will be apparent from the following detailed description taken in conjunction with the accompanying drawings. Here, it should be noted that a detailed description of known functions and configurations incorporated herein will be omitted so as not to obscure the subject matter of the present invention.

Hereinafter, exemplary embodiments of the present invention will be described herein below with reference to the accompanying drawings.

The present invention relates to a micro robot system and a capsule endoscope system for diagnosing a tubular digestive system, which will be described with reference to FIGS. 1 through 6.

Figure 1:
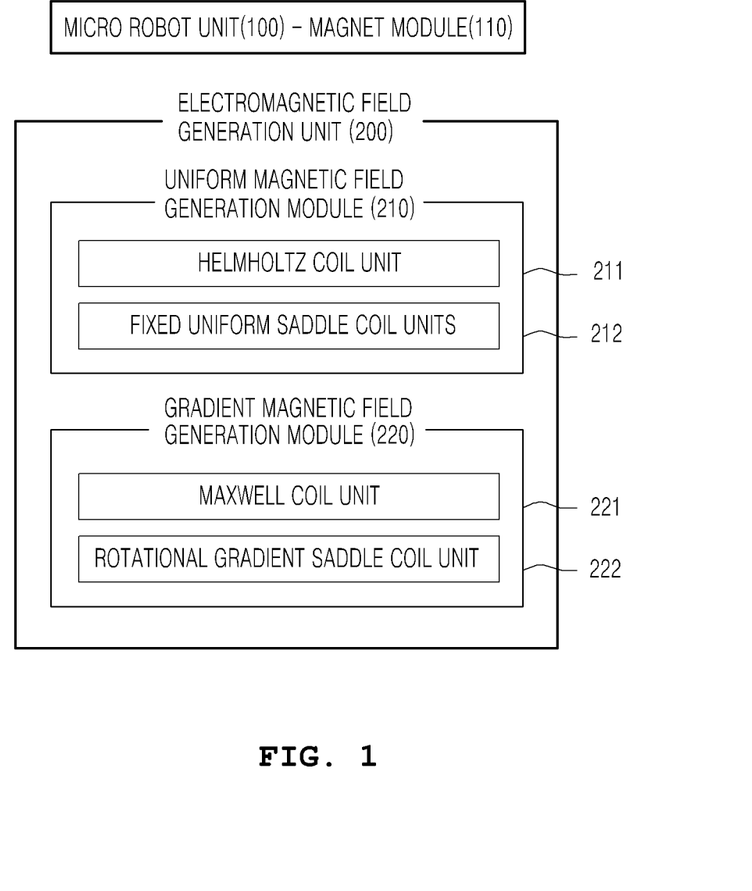
FIG. 1 is a block diagram illustrating a configuration of a micro robot system according to an exemplary embodiment of the present invention.

FIG. 1 is a block diagram illustrating a configuration of a micro robot system according to an exemplary embodiment of the present invention. The micro robot system according to the present invention includes a micro robot unit 100 and an electromagnetic field generation unit 200.

The micro robot unit 100 includes a magnet module 110 having a particular magnetization direction and proceeds, while rotating, along an organ's wall by processional rotating magnetic field. It should be noted that an apparatus such as a battery for providing power is included.

Figure 2:
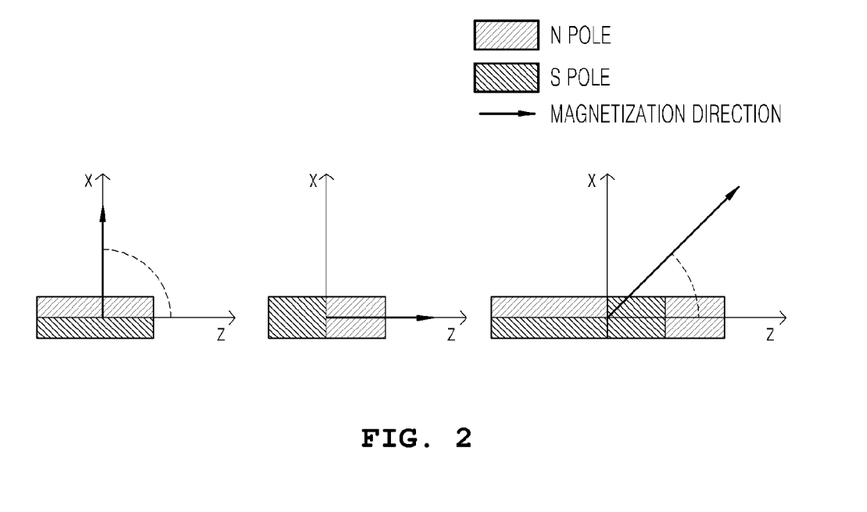
FIG. 2 is an exemplary view illustrating a method of generating a magnetization direction of a micro robot according to an exemplary embodiment of the present invention.

The magnet module 110 of the micro robot unit 100 includes a magnet having a particular magnetization direction, and various methods can be used to cause a magnet to have a particular magnetization direction. FIG. 2 is an exemplary view illustrating a method of generating a magnetization direction of a micro robot unit according to an exemplary embodiment of the present invention.

The magnetization direction is defined as a direction from an S pole to an N pole, and a particular magnetization direction may be created by adjusting the N and S poles of a magnet. The N pole and the S pole are configured to have different sizes or to be located differently to determine a certain magnetization direction and magnets that are magnetized in the certain direction are inserted to the micro robot unit 100 such that the micro robot unit 100 having the certain magnetization direction is formed.

Figure 3:
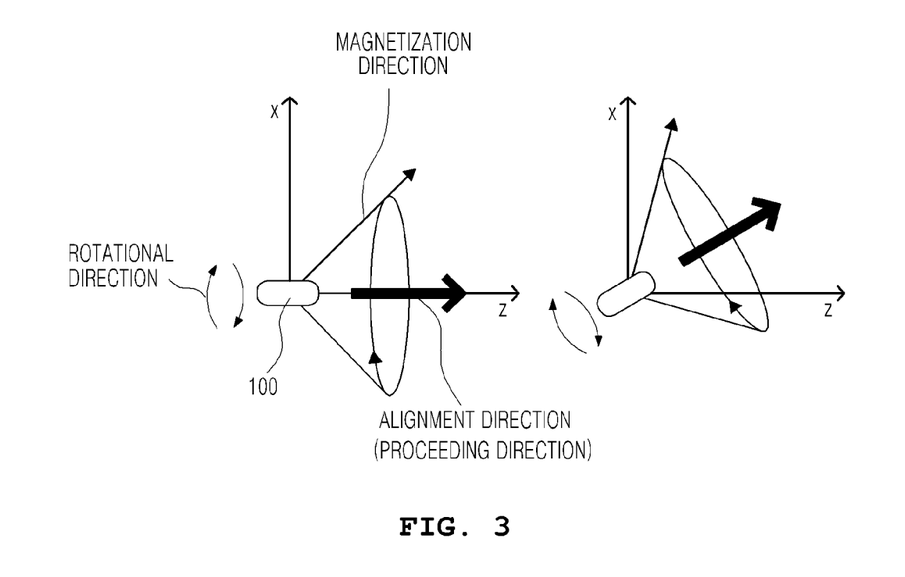
FIG. 3 is a correlation diagram for a magnetization direction, an alignment direction, and a rotational direction of a micro robot according to an exemplary embodiment of the present invention.

The magnetization direction relates to a processional rotating magnetic field of the micro robot unit 100, which will be described below. Referring to FIG. 3, if a z axis is a direction in which the micro robot 100 proceeds, a micro robot system that moves in a processional movement along the z axis is formed, while the magnetization direction becomes a slope edge of a circular cone.

The magnetization direction in three dimensional space is not important, however, the magnetization direction needs to be set such that a constant angle is maintained between the magnetization direction and an alignment direction (or proceeding direction) of the micro robot unit 100.

The electromagnetic field generation unit 200 sets the alignment direction of the micro robot unit 100 to have a constant angle with respect to the magnetization direction and generates a magnetic field in the magnetization direction, thereby driving the micro robot unit 100.

Figure 4A:
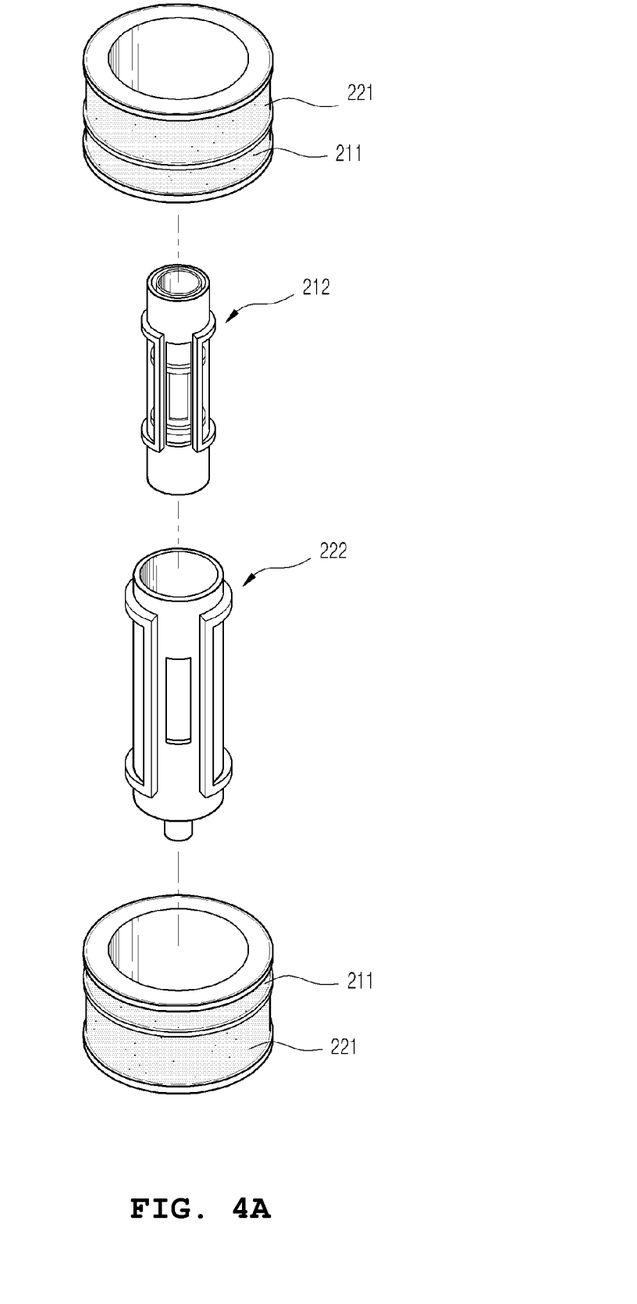
FIG. 4A is an exploded view illustrating a coil of an electromagnet field generation unit according to an exemplary embodiment of the present invention.
Figure 4B:
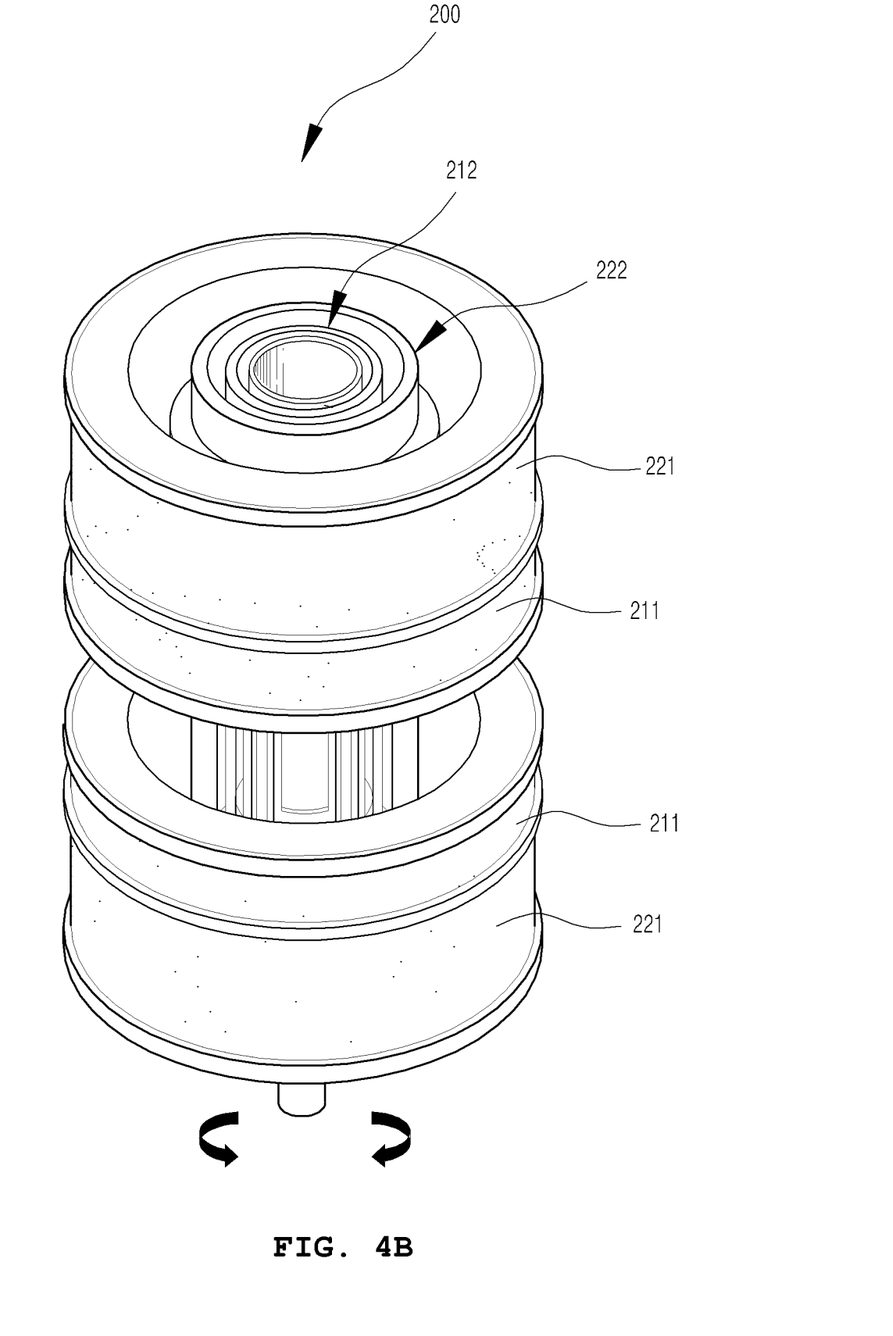
FIG. 4B is a coupled perspective view illustrating a coil of an electromagnet field generation unit according to an exemplary embodiment of the present invention.
Figure 4C:
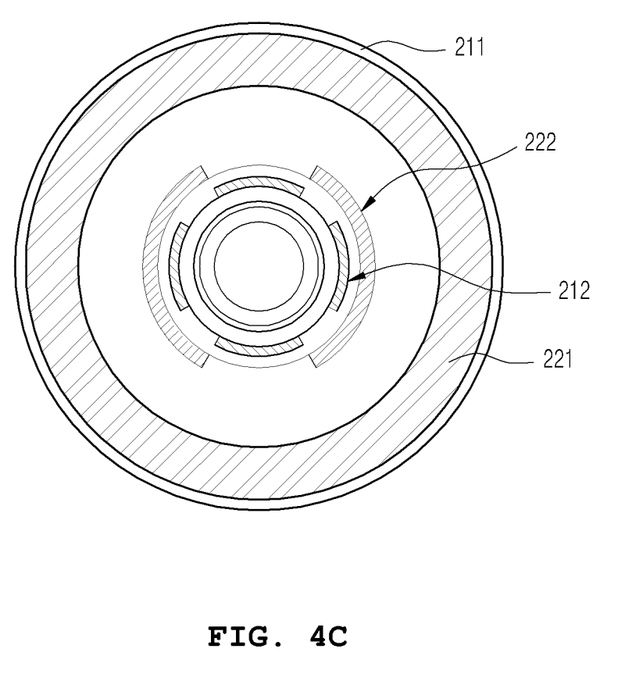
FIG. 4C is a cross sectional view illustrating a coil of an electromagnet field generation unit according to an exemplary embodiment of the present invention.

Referring to FIG. 4A, a pair of fixed Helmholtz coil units 211, a pair of fixed Maxwell coil units 221, two pairs of fixed uniform saddle coil units 212, and a pair of rotational gradient saddle coil units 222 are included.

The electromagnetic field generation unit 200 includes a uniform magnetic field generation module 210, which generates a constant magnet field in the alignment direction to align the micro robot unit 100 in the alignment direction and processionally rotates the micro robot unit 100 around the alignment direction, and a gradient magnetic field generation module 220, which generates a magnetic field having a constant acceleration to generate a constant driving force in a direction perpendicular to the alignment direction of the micro robot unit 100.

The uniform magnetic field generation module 210 includes the pair of the fixed Helmholtz coil units 211 and the two pairs of the fixed uniform saddle coil units 212, and the gradient magnetic field generation module 220 includes the pair of the Maxwell coil units 221 and the pair of the rotational gradient saddle coil units 222.

The uniform magnetic field generation module 210 generates a constant magnetic field in a certain direction on three dimensional space defined by x, y, and z axes by using the pair of the fixed Helmholtz coil units 211 and the two pairs of the fixed uniform saddle coil units 212, i.e., three pairs of fixed coils. Referring to FIG. 4A, when the pair of the Helmholtz coils 211 is installed to dispose opposite to each other and penetrating the z-axis, a magnetic field may be formed in a z axis direction. When the two pairs of the fixed uniform saddle coil units 212 are positioned on a plane perpendicular to the z axis and installed to face opposite and orthogonal to each other, magnetic fields may be respectively generates on the x and y axes that are perpendicular to the z axis. By adjusting intensity of current flowing in each axis, a magnetic field may be formed in any arbitrary direction in the three dimensional space.

The uniform magnetic field generation module 210 may be formed such that a pair of coils are configured to have the same current direction. The purpose of this is to align the micro robot unit 100 in a certain direction while determining the proceeding direction thereof. By controlling current applied to the pair of the coils, it is determined whether the proceeding direction of the micro robot unit 100 is a positive direction or a negative direction. The proceeding direction may be modified by changing a direction of current flowing through the coils.

A magnetic field generated by processionally rotating the micro robot unit 100 with respect to the alignment direction thereof is expressed as Equation 1 below.

$$B_x = \frac{[m\cos(\theta + \alpha) + m\cos(\theta - \alpha)]}{2} - \frac{[m\cos(\theta + \alpha) - m\cos(\theta - \alpha)]\cos\omega t}{2}$$ [Equation 1]

$$B_y = \frac{[m\sin(\theta + \alpha) - m\sin(\theta - \alpha)]}{2} +$$

$$B_z = m\sin\theta\sin\omega t \frac{[m\sin(\theta+\alpha)+m\sin(\theta-\alpha)]\cos\omega t}{2}$$

where θ represents the magnetization direction, α represents the alignment (or proceeding) direction, m represents magnetization intensity, and ω represent a rotational frequency when the micro robot unit 100 is rotated. Here, when ω is zero, the micro robot unit 100 is aligned in a certain direction.

The uniform magnetic field generation module 210 may rotate the micro robot unit 100 by quickly and smoothly changing the alignment direction of the coils. By using current control, a magnetic field generated on each axis is continuously changed through a frequency of ω so that the micro robot unit 100 may rotate around the axis.

When using a coil structure in the uniform magnetic field generation module 210, a constant magnetic field is generated such that only a function of aligning the micro robot unit 100 in a certain direction or a function of rotating the micro robot unit 100 is performed. Namely, when controlling the uniform magnetic field generation module 210 only, the micro robot unit 100 is only enabled to rotate in a certain direction at the same place.

Therefore, a magnetic field that provides a force to push forward the micro robot unit 100 is needed, for which the gradient magnetic field generation module 220 is used.

The gradient magnetic field generation module 220 may generate a driving force in any direction on the three dimensional space by using a pair of fixed coils and a pair of rotational coils. The coils included in the gradient magnetic field generation module 220 are designed such that a pair of coils has different current directions to each other, thereby providing a driving force to the micro robot unit 100.

Particularly, the coil included in the gradient magnetic field generation module 220 generates a magnetic field having a constant slope not only with respect to an axial direction thereof but also with respect to a direction perpendicular to the axial direction. While the uniform magnetic field generation module 210 generates a constant magnetic field, the gradient magnetic field generation module 220 forms a magnetic field having a constant slope to generate a force. Since a slope of the magnetic field is constant, a constant acceleration of the microrobot is generated, and the greater the slope is, the larger force is applied. A magnitude of the slope of the magnetic field may be adjusted by intensity of current.

Referring to FIG. 4A, when the pair of the Maxwell coil units 221 is installed to oppose each other and penetrate the z axis, a magnetic field may be formed in the z axis direction. When the pair of the rotational gradient saddle coil units 222 is installed on a rotational member with an arbitrary axis as a rotation axis thereof, magnetic fields having constant slopes with respect to axes perpendicular to the z axis can be respectively formed. Particularly, although the gradient saddle coil units 222 comprise a pair, since the gradient saddle coil units 222 can be rotated, a magnetic field having a constant slope in any arbitrary direction on an x-y plane can be formed. Therefore, by adjusting the intensity of current in each axis, a driving force may be generated in any arbitrary direction on a z-r plane on the three dimensional space, wherein an r axis is an alignment axis of the rotational gradient saddle coil unit. Since the r axis rotates 360 degrees, an entire three dimensional space can be covered.

Generally, when the magnetization direction coincides with the proceeding direction, a component in the magnetization direction perpendicular to the proceeding direction does not exist. Therefore, by respectively controlling the slope of the magnetic fields generated in the two pairs of coils, the driving force may be generated only in the proceeding direction such that the micro robot unit 100 moves in a forward direction.

When the magnetization direction is different from the proceeding direction, as in the present system, the magnetization direction may be divided into a component in the proceeding direction and a component in a direction perpendicular to the proceeding direction. Therefore, by respectively controlling the slopes of the magnetic fields generated by the two pairs of coils, a driving force in the proceeding direction is generated by the component in the proceeding direction to enable the micro robot 100 to move in a forward direction and a driving force in a direction perpendicular to the proceeding direction is generated by the component in the direction perpendicular to the proceeding direction to enable the micro robot 100 to push the organ's wall.

Generally, a magnetization direction and intensity of the micro robot unit 100 are fixed such that a force generated in a particular direction may be controlled by controlling current generated in the two coils. Therefore, the micro robot unit 100 may proceed forward while rotating along the organ's wall.

Figure 5A:
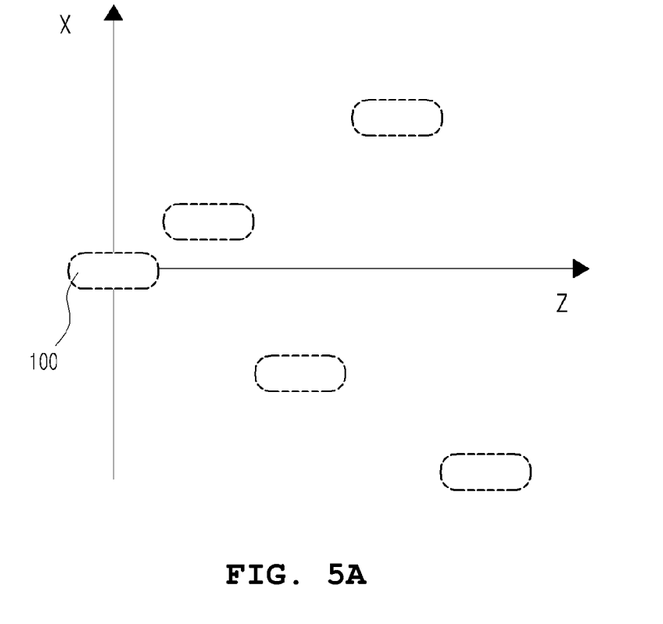
FIG. 5A is a schematic view illustrating proceeding of a micro robot according to an exemplary embodiment of the present invention.

FIG. 5A is a schematic view illustrating proceeding of the micro robot unit 100 according to an exemplary embodiment of the present invention. Since the micro robot unit 100 has a magnetization direction having a certain angle with respect to the z axis, which is the proceeding direction thereof, a driving force applies to the z axis that is the proceeding direction thereof and the x axis that is perpendicular to the z axis. Therefore, the micro robot unit 100 moves along the z axis while rotating in a cone-shaped path.

Figure 6:
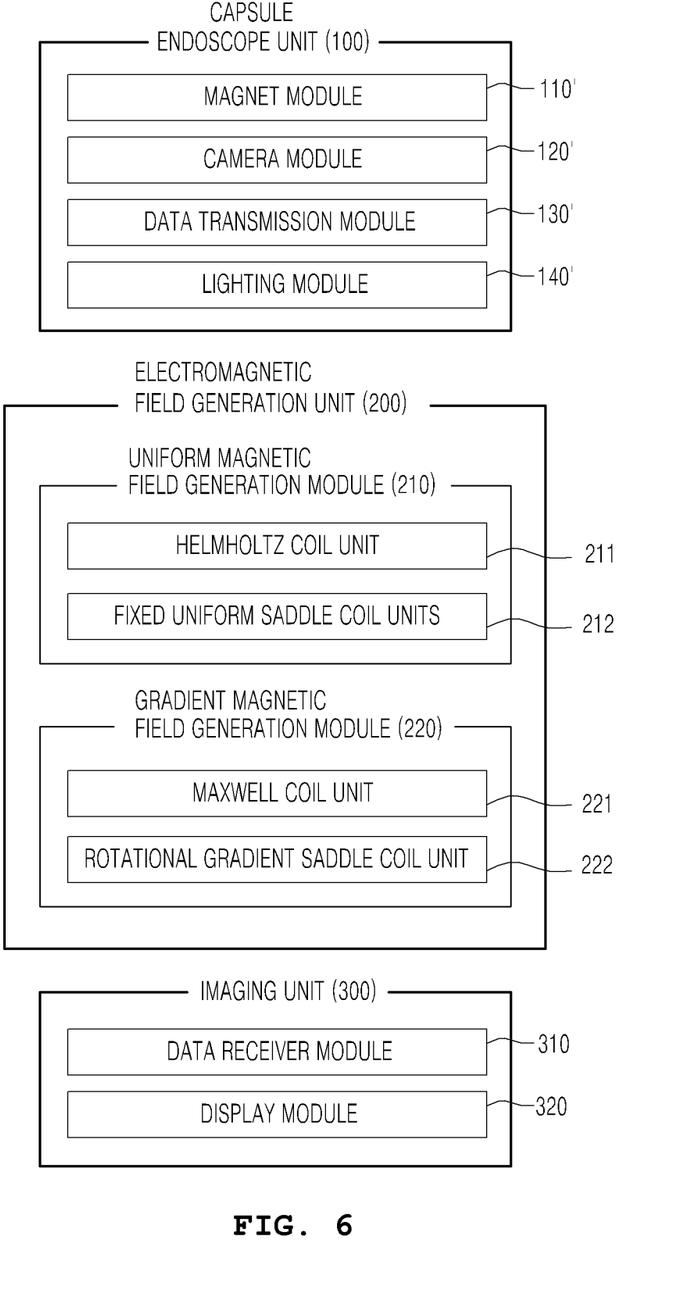
FIG. 6 is a block diagram illustrating a configuration of a capsule endoscope system for diagnosing a tubular digestive system according to an exemplary embodiment of the present invention.

FIG. 6 is a block diagram illustrating a configuration of a capsule endoscope system for examining a tubular digestive system according to an exemplary embodiment of the present invention.

The capsule endoscope system for examining a tubular digestive system according to an embodiment of the present invention includes a capsule endoscope unit 100', an electromagnetic field generation unit 200 and an imaging unit 300.

The capsule endoscope unit 100' includes a magnetic module 110' having a certain magnetization direction and a micro robot that proceeds, while rotating, along the organ's wall by a processional rotating magnetic field. The capsule endoscope unit 100' further includes a camera module 120' and a data transmission module 130'. It should be noted that an apparatus such as a battery for providing power is included.

Here, when installing the camera module 120', a lighting module 140' is installed together to aid photographing. The lighting module 140' is used to ease photographing in a dark area and generally uses a light emitting diode (LED) lamp; however, the present invention is not limited to this.

The camera module 120' moves along the organ's wall, photographs a disease on the wall, and transmits an image data photographed by the camera module 120' and location information of the capsule endoscope unit 100' to the imaging unit 300.

The capsule endoscope unit 100' includes the camera module 120' and the data transmission module 130' that are typically used in the conventional capsule endoscope; however, unlike the conventional capsule endoscope that does not have a self-driving force, the capsule endoscope unit 100' is characterized in that, by including a magnet having a certain magnetization direction, the capsule endoscope unit 100' may be controlled by a user by an electromagnetic field applied from an outside.

Particularly, the present system proceeds along an inner surface of the wall of the digestive system to examine the disease on the wall, and the camera is installed, not in a front/rear of the cylindrical capsule endoscope along the longitudinal direction thereof, but along a wall of the cylindrical capsule endoscope. Here, the camera can be of any type. A camera, which is generally used for the capsule endoscope, may be sufficient.

Even when the camera is installed along the wall of the capsule endoscope unit 100' having a cylindrical shape, good quality photography could not be obtained unless the camera does not proceed and rotated along the wall. Therefore, the capsule endoscope unit 100' includes a magnet having a particular magnetization direction. Various methods may be used to produce a magnet having a particular magnetization direction, which has already described above with reference to FIG. 2.

The magnetization direction is defined as a direction from the S pole to the N pole, and a particular magnetization direction may be formed by adjusting the N and S poles of a magnet. The N pole and the S pole are configured to have different sizes or to be located differently to determine a certain magnetization direction and a magnet that is magnetized in the certain direction is inserted to the capsule endoscope unit 100' such that the capsule endoscope unit 100' having the certain magnetization direction is formed.

The magnetization direction relates to a processional rotating magnetic field of the micro robot unit 100, which will be described below. Referring to FIG. 3, if a z axis is a direction in which the capsule endoscope unit 100' proceeds, a capsule endoscope system that moves in a processional movement along the z axis is formed, while the magnetization direction becomes a slope edge of a circular cone.

The magnetization direction in the three dimensional space is not important; however, the magnetization direction needs to be set such that a certain angle is maintained between the magnetization direction and the alignment direction (or proceeding direction) of the capsule endoscope unit 100'. Therefore, the present invention is not limited to the above described method of specifying the magnetization direction.

The electromagnetic field generation unit 200 sets the alignment direction of the capsule endoscope unit 100' to have a certain angle with respect to the magnetization direction and produces a magnetic field in the alignment direction to drive the capsule endoscope unit 100', which is the same as in the micro robot system.

Figure 5B:
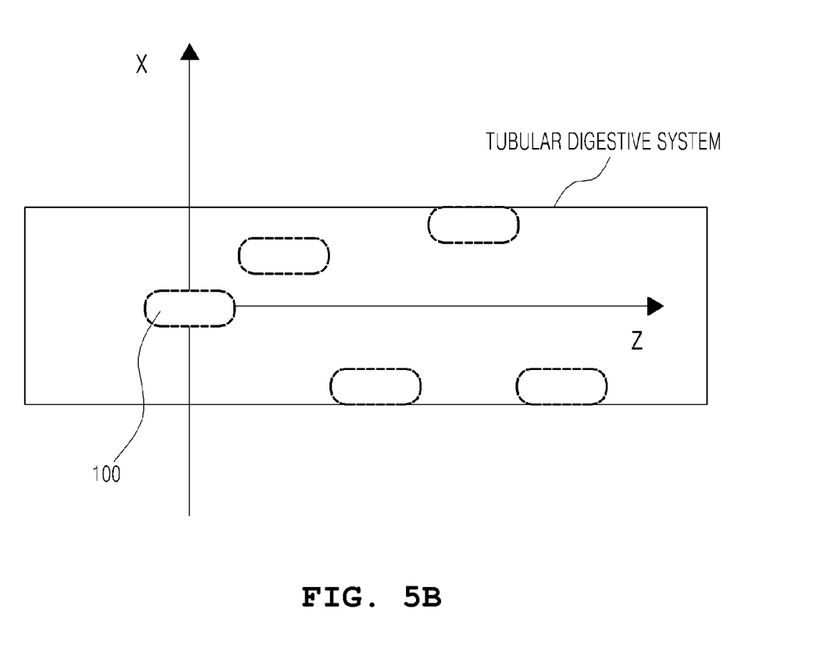
FIG. 5B is a schematic view illustrating proceeding of a micro robot within a tubular digestive system.

However, the present system is a capsule endoscope system for examining a tubular digestive system, and referring to FIG. 5B, when assuming that a large square box represents a cross section of the tubular digestive system, the capsule endoscope unit 100' may proceed, while rotating, along the z axis, which is the same as the proceeding direction of the micro robot unit 100. However, unlike FIG. 5A, the movement of the capsule endoscope unit 100' may not spread out but is trapped in the tubular digestive system to rotate and proceed along the wall.

The imaging unit 300 receives an image obtained by the capsule endoscope unit 100' and a position of the capsule endoscope to be displayed. The imaging unit 300 includes a data receiver module 310 and a display module 320.

The data receiver module 310 receives the image obtained by the capsule endoscope unit 100' and an operating position of the capsule endoscope unit 100' and the display module 320 displays the image received from the data receiver module 310. In case of an endoscope system, the imaging unit 300 included in a general endoscope system, which displays the image photographed in real time by the capsule endoscope while moving is used.

An apparatus for tracking the position of the capsule endoscope may be further included. An apparatus, which is used in a typical method of tracking a location of the micro robot, may be used and a method of tracking a location of the capsule endoscope using a bi-plane x-ray may be used.

According to the present invention, by generating the processional rotating magnetic field with respect to the alignment direction while the magnetization direction and the alignment direction of the micro robot having a certain angle therebetween, a micro robot driving system in which the micro robot may rotate with respect to the alignment direction and proceed forward while pushing the organ's wall may be provided.

In addition, by installing the camera along the longitudinal direction of a capsule cylinder of the micro robot, namely, the wall of the capsule cylinder, the disease on the wall of the tubular digestive system may be examined.

In the above, although the embodiments of the present invention have been described with reference to the accompanying drawings, a person skilled in the art should apprehend that the present invention can be embodied in other specific forms without departing from the technical spirit or essential characteristics thereof. Thus, the embodiments described above should be construed as exemplary in every aspect and not limiting.

What is claimed is:

1. A micro robot system movable on three dimensional space, the micro robot system comprising:
    a micro robot unit including a magnet module having a certain magnetization direction and rotating and proceeding along a wall by a processional rotating magnetic field; and
    an electromagnetic field generation unit setting an alignment direction of the micro robot unit to have a certain angle with respect to the magnetization direction and generating a magnetic field in the alignment direction to drive the micro robot unit,
    wherein the electromagnetic field generation unit includes
        a pair of Helmholtz coil units disposed to face opposite to each other and penetrating a certain axis on the three dimensional space,
        a pair of Maxwell coil units disposed to face opposite to each other and penetrating the certain axis,
        two pairs of fixed uniform saddle coil units located on a plane perpendicular to the certain axis and fixedly installed to be orthogonal to each other, and
        a pair of rotational gradient saddle coil units installed on a rotating member and rotating on the certain axis.

2. A capsule endoscope system movable on three dimensional space, the capsule endoscope system comprising:
    a capsule endoscope unit including a magnet module having a certain magnetization direction and rotating and proceeding along a wall by a processional rotating magnetic field;
    an electromagnetic field generation unit setting an alignment direction of the capsule endoscope to have a certain angle with respect to the magnetization direction and generating a magnetic field in the alignment direction to drive the capsule endoscope unit; and
    an imaging unit receiving and displaying an image photographed by the capsule endoscope unit and a location of the capsule endoscope,
    wherein the electromagnetic field generation unit includes a pair of Helmholtz coil units disposed to face opposite to each other and penetrating a certain axis on the three dimensional space, a pair of Maxwell coil units disposed to face opposite to each other and penetrating the certain axis, two pairs of fixed uniform saddle coil units located on a plane perpendicular to the certain axis and fixedly installed to be orthogonal to each other, and a pair of rotational gradient saddle coil units installed on a rotating member and rotating on the certain axis.

3. The capsule endoscope system according to claim 2, wherein the capsule endoscope unit comprises:

a camera module moving along a wall of an organ and obtaining disease images on the wall; and a data transmission module transmitting an image data photographed by the camera module and location information of the capsule endoscope unit to the imaging unit.

4. The capsule endoscope system according to claim 3, wherein the camera module includes a predetermined camera installed on a wall of a body of a capsule endoscope having a cylindrical shape.

5. The capsule endoscope system according to claim 3, wherein the capsule endoscope unit further comprises:

a lighting module installed on a wall of a body of a capsule endoscope having a cylindrical shape and configured to emit light toward a photographing direction when the camera module obtains an image.

6. The capsule endoscope system according to claim 2, wherein the imaging unit comprises:

a data receiver module receiving the image obtained by the capsule endoscope unit and an operating position of the capsule endoscope unit; and a display module displaying the image received by the data receiver module.

* * * * *